United States Patent [19]

Nordahl

[11] 4,345,334
[45] Aug. 17, 1982

[54] REDUCED-CROSS TALK TELEMETRY SYSTEM AND METHOD OF MANUFACTURE THEREOF

[75] Inventor: John G. Nordahl, Lexington, Mass.

[73] Assignee: American Optical Corporation, Southbridge, Mass.

[21] Appl. No.: 793,985

[22] Filed: May 5, 1977

[51] Int. Cl.$^3$ .......................................... H04B 7/015
[52] U.S. Cl. ...................................... 455/50; 455/45; 455/63; 370/120; 340/870.28; 340/870.26
[58] Field of Search ...................... 325/52, 53, 55, 56, 325/57, 65; 343/200; 340/182, 189 M, 207 R; 455/50, 51, 52, 53, 54, 63, 65; 370/69, 71, 73, 75, 76

[56] References Cited

U.S. PATENT DOCUMENTS

| | | | |
|---|---|---|---|
| 2,298,409 | 10/1942 | Peterson | 455/45 |
| 3,258,694 | 6/1966 | Shepherd | 370/69 |
| 3,572,316 | 3/1971 | Vogelman | 340/207 R |
| 3,639,907 | 2/1972 | Greatbatch | 340/189 M |
| 3,757,220 | 9/1973 | Abel | 370/69 |
| 3,965,300 | 6/1976 | Markl | 370/69 |
| 3,986,498 | 10/1976 | Lewis | 340/207 R |

OTHER PUBLICATIONS

Radiotelemetry System for Fetal Monitoring, by Castelfiori, Conference-International Symposium on Biotelemetry, Nijmegen, Netherlands (May 5–8, 1971), pp. 237–245.
An Eight Channel Micropowered PAM/FM Biomedical Telemetry System, by Olsen et al., NTC '71 Record, pp. 308–311.
Telemetry of Venous Blood Pressure at Rest and at Muscle Activity During Running, by Rieckert et al., Conference: International Symposium on Biotelemetry, Netherlands (May 5–8, 1971), pp. 179–182.

Primary Examiner—Tommy P. Chin
Attorney, Agent, or Firm—Jeremiah J. Duggan

[57] ABSTRACT

Method and apparatus for providing a multi-channel telemetry system in which the fundamental frequencies of the transmit-receive channels of the system are selected from a series of tentative fundamental frequencies. The successive fundamental frequencies in series therewith each having the same geometric relation to the immediately preceding and immediately succeeding fundamental frequency such that potentially interfering cross talking channels in similar geometric relation may be identified and eliminated.

9 Claims, 5 Drawing Figures

REDUCED-CROSS TALK TELEMETRY SYSTEM AND METHOD OF MANUFACTURE THEREOF

BACKGROUND OF THE INVENTION

The invention relates generally to telemetry systems and more particularly to channel assignments associated with telemetry systems. More particularly, still, the invention relates to channel frequency assignments for multichannel telemetry systems for the purpose of reducing cross talk.

Telemetry systems basically comprise means for transmitting information from one location to a "remote" receiving location. The transmission is via radio waves rather than through a direct physical connection and it is with the former type of telemetry system that the present invention is principally involved.

Telemetry systems may comprise only one or a large number of transmit-receive channels. In the event two or more transmit-receive channels are used, it is possible for spurious electrical signals appearing in the transmitted frequency spectrum at a frequency closely adjacent that of another receiver fundamental channel frequency of the telemetry system to interfere with and/or override the information normally conveyed by the proper transmitter. The present invention is particularly concerned with telemetry systems having a relatively large number of transmit-receive channels and in which the problem of cross talk is created by spurious signals originating with the various other channels of the telemetry system.

The spurious signals from other telemetry channels which may cause the problem of cross talk can arise from the manner in which the channel or carrier frequency for the respective channels is developed. For example, it is common to generate the carrier frequency for a particular channel by multiplying a respective basic frequency obtained from a crystal oscillator or the like. In the process of frequency multiplication, various harmonics of the basic oscillator frequency are produced and these harmonics may be of such frequency and strength to interfere with fundamental frequencies of other telemetry channels.

In a significant exemplary situation, multi-channel telemetry systems are finding increasing use in hospitals and similar health-care facilities for the purpose of transmitting physiological information from a patient to a remote receiver. In such systems, the patient is normally ambulatory and may move about the hospital. The various receivers for the respective channels may all be connected at a central location to an antenna system installed within the hospital. The receiver associated with each telemetry channel is appropriately identified and may be extended to a display or recording means for visual and/or written read-out of the particular information. However, because of the aforementioned problem of cross talk, it is possible and not uncommon for the information signal from a patient on a particular telemetry channel to be obliterated or replaced by a spurious signal associated with a different patient and telemetry channel. This situation may arise where the patient on the channel being monitored moves relatively distant from the antenna system and a patient wearing a transmitter having spurious signals approximating the fundamental frequency of the channel being monitored moves relatively close to the antenna system such that the spurious signal becomes dominant.

It will be appreciated that distortion of information being received from a particular patient may be particularly undesirable and more importantly, substitution of another patient's physiological information therefor can create a potentially dangerous situation. Although certain filtering techniques and equipment may substantially reduce this problem, their relatively high cost comprises a significant deterrent to their use. In order to avoid the interference and/or confusion which may result from cross talk, efforts have been made to assign the frequencies of the respective channels such that the cross talk is either minimized or eliminated.

The usual practice has been to identify a series of tentative channel frequencies spaced from one another at random or arithmetically spaced intervals. This requires individual inspection of each tentative channel to determine the absence of cross talk from spurious signals generated by the harmonics of the respective basic frequencies of the respective oscillators. Such techniques have been extremely time-consuming and have generally not made optimum use of the available operating band.

Accordingly, it is a principal object of the present invention to provide an improved multi-channel telemetry system and a method of manufacture thereof which, in a relatively economic manner, optimizes the assignment and utilization of channel frequencies within a band with a minimum of cross talk.

This and other objects will be in part obvious and in part pointed out in greater detail hereinafter.

SUMMARY OF THE INVENTION

In accordance with the present invention, there is provided an improved multi-channel telemetry system and method of manufacture thereof, in which the fundamental frequencies of the transmit-receive channels of the system are selected from a series of tentative fundamental frequencies, the successive fundamental frequencies in the series each having the same geometric relation to the immediately preceding fundamental frequency in the series whereby the determination of the relationship(s) therewith of potentially interfering cross-talking signals also having a geometric relation with certain fundamental frequencies in the series is facilitated.

The present invention finds particular utility in telemetry systems in which the fundamental frequency of each operating or transmit channel comprises a constant multiple of a respective basic oscillator frequency whereby spurious signals resulting from various multiples of each of the basic frequencies are present and may cross-talk to certain receive channels tuned thereto.

The geometric relation between the respective tentative fundamental frequencies is selected such that the frequencies of substantially all of the aforementioned spurious signals differ sufficiently from substantially all of the receiver channels in the series to avoid cross-talk therewith.

In order to determine a substantially optimum multiplying factor as the geometric relation between successive channel frequencies, an approximate multiplying factor is first determined. The effects of successive small adjustments to the approximate value are analyzed to arrive at a preferred or optimum value, that optimum value having been seen to exist when the absolute frequency margin is maximized for whichever of the spurious components has the smallest frequency margin between each of the spurious components and the fundamental receiver channel. Each receiver normally has about the same rejection frequency limits (i.e. about 500 kHz in the illustrated embodiment) at a predetermined threshold value (i.e. about −70 db in the illustrated embodiment) and the approximate multiplying factor may be determined as one which would yield the maximum number of channels in the band of interest without overlap of the rejection limits of adjacent channels, particularly at the lower end of the band.

In a particular embodiment in which the basic oscillator frequency for each channel is multiplied by a factor of 12 to obtain the respective transmitter channel fundamental frequency and the ratio of the upper-end frequency to the lower-end frequency of the predetermined band is about 1.25 to 1 such that the spurious signals within the range of 10/12th to 14/12th of the various basic frequencies may occur within the predetermined band, an approximate multiplying factor commensurate with about 61–62 channels was analyzed and resulted in a substantially optimum geometric relation between the respective tentative fundamental frequencies of 1.00355175652. This arrangement is particularly suited for the 174 MHz to 216 MHz bandwidth utilized by medical telemetry and provides 61 tentative channels.

The aforementioned assignment of fundamental frequencies for the various telemetry channels is, of course, only tentative and those channels actually selected for use may be further limited to those which are substantially free of interference from sources other than the transmitter-generated spurious signals.

BRIEF DESCRIPTION OF THE PREFERRED EMBODIMENT

Figure 1:
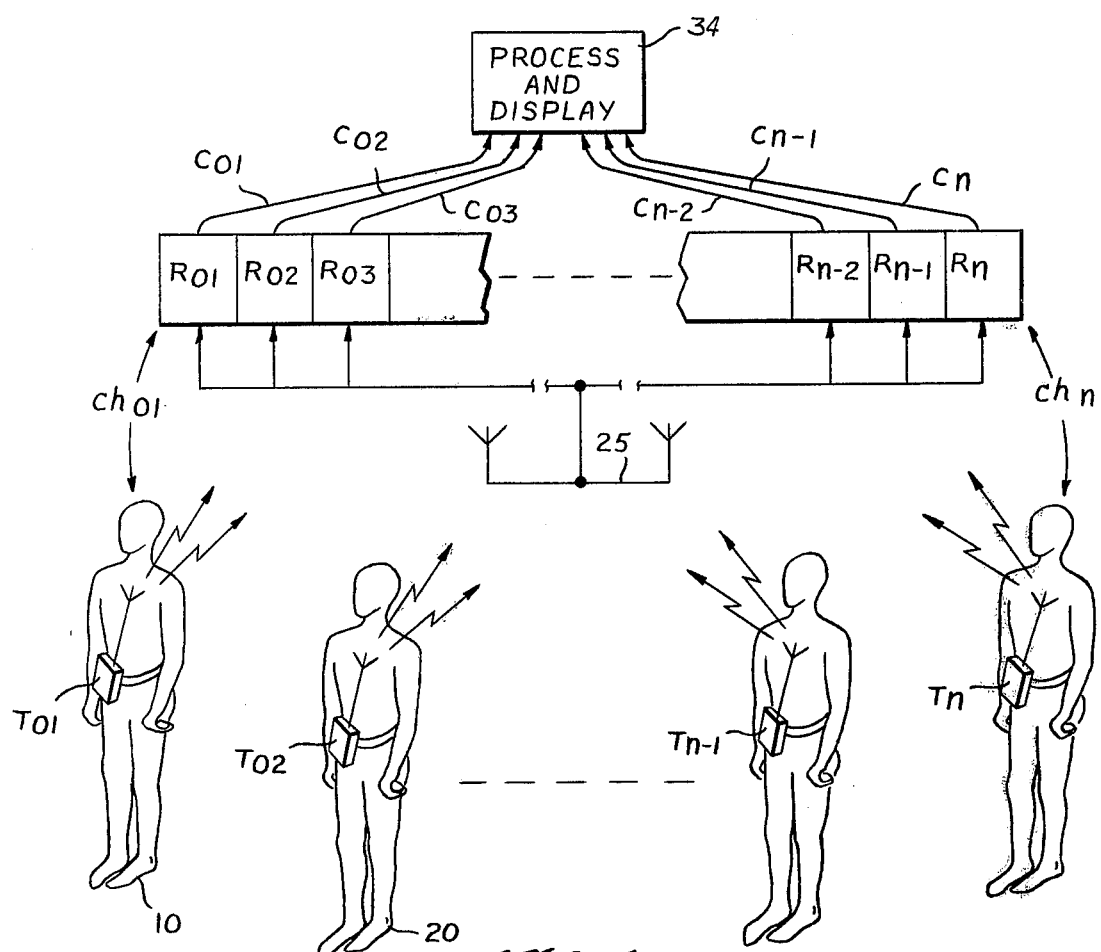
FIG. 1 is a diagrammatic illustration of a multichannel medical telemetry system incorporating the present invention.

Referring now to FIG. 1, there is illustrated a multichannel medical telemetry system comprised of "n" possible channels. Each telemetry channel is comprised of a respective transmitter, such as $T_{01}$, $T_{02}$ etc. and a respective receiver such as $R_{01}$, $R_{02}$ etc. A patient 10 wears transmitter $T_{01}$, a patient 20 wears transmitter $T_{02}$, etc. Each transmitter may be monitoring one or more physiological waveforms of the respective patient. The patient's electrical heart signals (ECG) comprise one particularly significant example of a monitored physiological waveform.

All "n" receivers associated with the respective "n" telemetry transmitters are connected to a common antenna system 25. The antenna system 25 may comprise a series of antennas approximately positioned about a portion of a hospital with appropriate passive couplers to maintain impedance matching and wide band amplifiers as necessary (not shown). The outputs $C_{01}$ and $C_n$ from the respective receivers $R_{01}$ ... $R_n$ may be connected to a central processing and display unit 34 which may be centrally located for providing visual display of the respective patient's physiological information. Such display may be real time and/or recorded. Further, unit 34 may process each of the respective received signals to provide an alarm or some other appropriate response.

Figure 2:
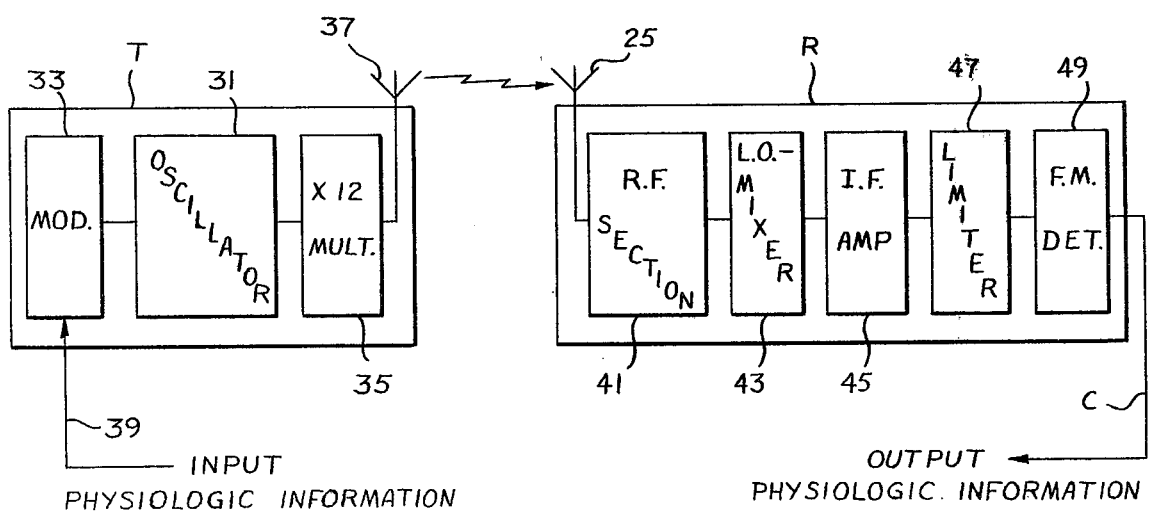
FIG. 2 is a generalized diagrammatic representation of a transmitter and receiver in the telemetry system of FIG. 1.

Each of the "n" channels in the telemetry system has a particular fundamental frequency different from that of the other channels in the system. Referring to FIG. 2, there is illustrated an exemplary frequency-modulated (FM) transmitter T and a corresponding FM receiver R. The block diagrams of the transmitter and receiver, T and R respectively, have been greatly simplified to show substantially only those component portions thereof required for an understanding of the present invention.

Transmitter T includes a varactor modulator 33 which acts on a crystal oscillator 31 having its output connected to a "12-times" (i.e. 3.2.2.1) frequency multiplier 35 which is, in turn, coupled to a transmitting antenna 37. A modulating input, here represented as an ECG signal, is applied via line 39 to the modulator 33 for modulating the basic frequency provided by the oscillator 31. In the example of the present embodiment, a commonly-assigned VHF bandwidth between 174–216 MHz for medical telemetry is utilized. Because the crystals available for use in the present oscillators are normally limited to maximum frequencies of less than about 20 MHz, it is necessary to multiply the carrier frequency (in this case by a factor of 12) to obtain the actual fundamental carrier frequency of the respective channel.

The frequency multiplier 35, in addition to the fundamental carrier frequency, also radiates energy at various other harmonics of the basic frequency provided by oscillator 31. Stated another way, this additional energy will be radiated at frequencies which are at 1/12 increments (above and below) of the fundamental carrier frequency. In other words, if the fundamental channel frequency appearing at the output of multiplier 35 is considered as 12/12th, these additional radiations (hereinafter termed spurious signals) will occur at frequencies which are 11/12th, 10/12ths, 9/12ths, etc. and 13/12ths, 14/12ths, 15/12ths, etc. of the fundamental channel frequency. Thus, if the basic frequency from oscillator 31 was 15 MHz and the fundamental channel frequency was then 180 MHz (12×15), the aforementioned spurious radiations would occur at 165 MHz (i.e. 11/12th×180), 150 MHz (i.e. 10/12th×180), etc. and 195 MHz (i.e. 13/12ths×180), 210 MHz (i.e. 14/12ths×180), etc.

The aforementioned spurious signals are associated with each of the fundamental channel frequencies in the telemetry system. Inasmuch as the basic frequency from oscillator 31 is frequency-modulated by the ECG signal prior to the multiplication by "times-12" multiplier 35, the various spurious signals will similarly be modulated in accordance with the input ECG signal. It is principally these spurious signals which create the problem addressed by the present invention.

The receiver R is a conventional FM receiver which receives the transmitted signal through the antenna system 25. The signal appearing on antenna system 25 is then coupled to an RF section 41, which, in turn, is coupled to a local oscillator-mixer 43, which, in turn, is coupled to an intermediate frequency amplifier 45, which, in turn, is coupled to a limiter 47, which, in turn, is coupled to an FM detector 49 and from which the ECG modulating signal is detected and de-modulated and provided as an output signal on conductor C.

As previously mentioned, the assigned bandwidth within which the present telemetry system must operate is 174-216 MHz. Stated as a frequency ratio, the assigned band has a ratio of about 1:1.25 (i.e. 174:216). With this particular frequency ratio to the assigned bandwidth and recalling that the various spurious signals associated with any particular fundamental channel frequency comprise 1/12th increments of that particular frequency, it will be appreciated that two spurious signals associated with any particular fundamental frequency will occur within the particular assigned band. Although in some instances a third spurious signal might be closely adjacent the limits of the band, such third spurious signals will fall outside the band. It will be further appreciated that the number of spurious signals which may pose a problem within a particular band will depend upon the width of the band and the factor of frequency multiplication required to obtain a fundamental channel frequency from the respective basic oscillator frequency, such frequency multiplication determining the harmonics which constitute the respective spurious signals. Although the problem of potentially cross-talking spurious signals is reduced by reducing the number of spurious signals within the band (i.e. increase the spacing between oscillation multiples), the upper limit to the basic frequency of oscillator 31 is usually determined by the crystal, thereby limiting the extent of any such reduction of spurious signals.

Referring now more particularly to the inventive principles of the present invention, it has been recognized that by spacing successive fundamental frequencies of the channels within an assigned band at a substantially constant geometric relation to the respective immediately preceding fundamental frequency, an analysis of a single general-case fundamental frequency and the several spurious signals which may interfere therewith is similarly applicable to each and every one of the remaining fundamental frequencies in the series within the assigned band. Accordingly, by then adjusting the geometric relation between successive fundamental frequencies to optimize the frequency displacement between the several potentially interfering spurious signals and the fundamental frequency in the general-case situation, the displacement of other potentially interfering spurious signals with respective other fundamental frequencies in the assigned band is similarly optimized. This technique greatly simplifies the task of assigning frequencies to the successive channels in the operating band by obviating the need to analyze each fundamental frequency and its attendant spurious signals in an individual manner. This result obtains because of the geometric relationship between successive fundamental frequencies and the commensurate geometric relation of the various spurious signals with the respective fundamental frequencies.

Figure 3:
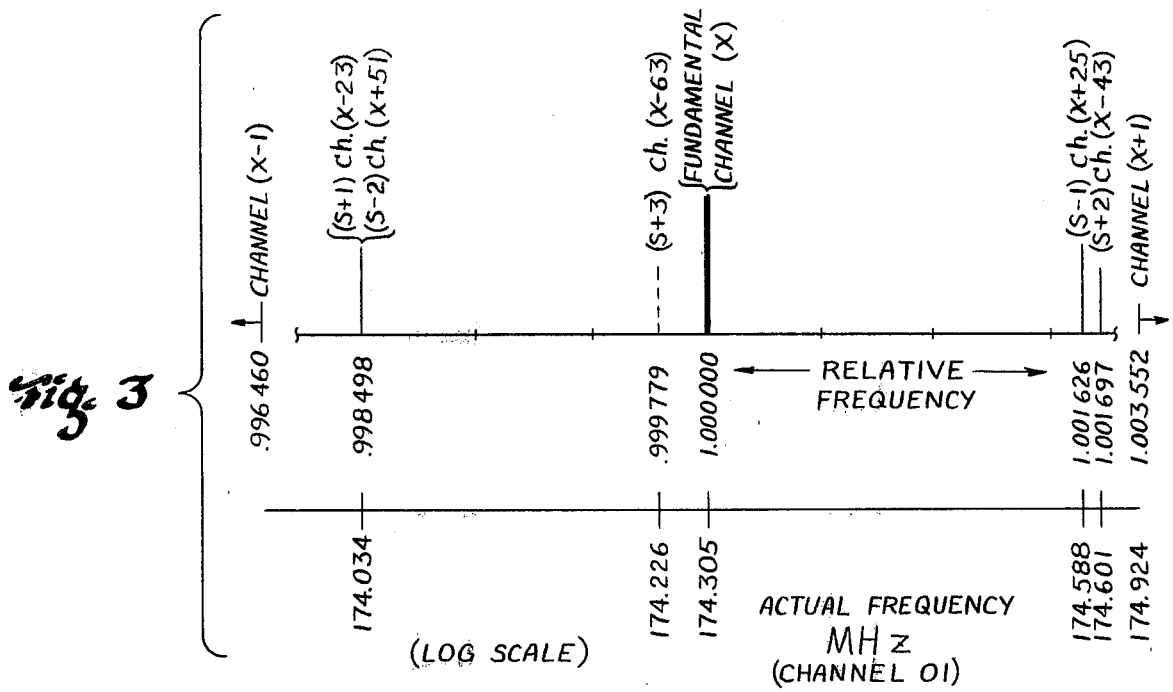
FIG. 3 is a frequency-spectrum plot of a representative, general-case telemetry channel optimized for the illustrated embodiment and showing those spurious signals arising from other channels and which are positioned most closely thereto in the frequency spectrum, the frequency base of the plot being a pair of logarithmic scales, the upper scale being calibrated in terms of relative frequency and the lower scale being calibrated in terms of actual frequency.
Figure 4:
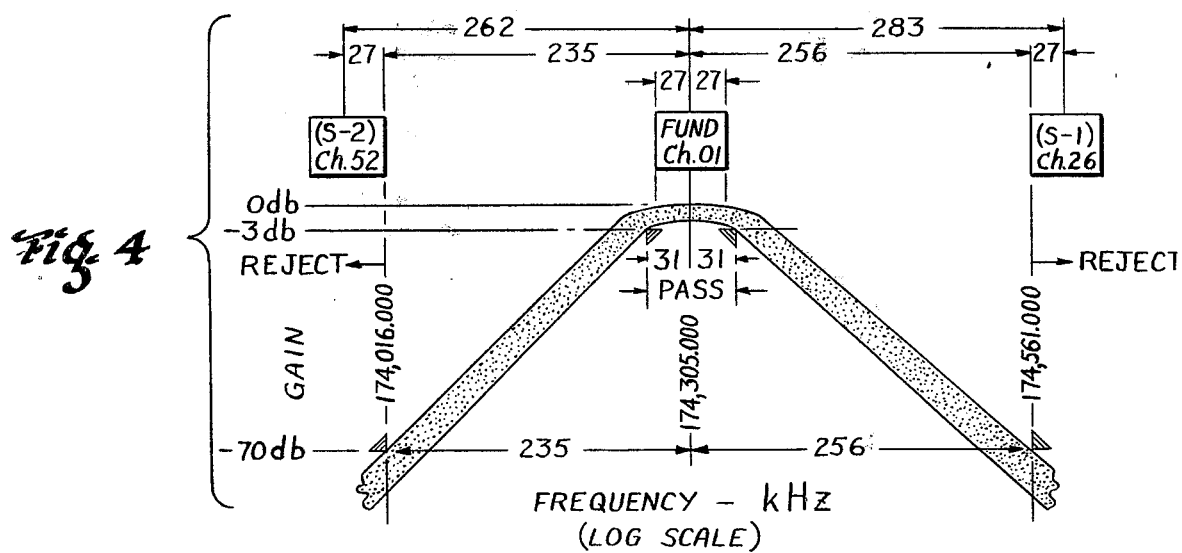
FIG. 4 is a plot of the selectivity curve (frequency vs gain) of a representative telemetry receiver, the frequency base thereof corresponding with that illustrated in FIG. 3 immediately thereabove.

Referring to FIGS. 3 and 4, there is illustrated in FIG. 3 an optimized general-case situation in accordance with the present illustrative bandwidth and its upper end-to-lower end ratio and with the particular frequency-multiplication factor of the present embodiment, as well as in conjunction with the limitations and capabilities of the particular receivers R utilized in the present embodiment and illustrated in FIG. 4. Each receiver R possesses the selectivity (frequency vs. gain characteristics) illustrated in FIG. 4. The receiver's sensitivity is 2 microvolts or better (for 20 db quieting) within about ±30-35 kHz of the exact specified fundamental channel frequency when driven from a 50 ohm unmodulated test generator connected to the antenna terminals. Further, this receiver sensitivity bandwidth is not narrowed by more than about ±0.002% by the environmental conditions experienced by the receiver. Further still, the selectivity of each receiver is such that five millivolt interference test signals applied at frequencies of 0.1482% below and 0.1606% above the specified fundamental channel frequency will be rejected. These rejection limits correspond approximately with the −70 db threshold illustrated in FIG. 4. The acceptance vs. rejection capabilities of each receiver are substantially as illustrated in FIG. 4.

The spurious signals associated with the generation of any particular fundamental frequency may be of sufficient magnitude to be detected by a receiver tuned any closer to their respective frequencies than the −70db limits of the frequency rejection curve illustrated in FIG. 4. Therefore, to prevent cross talk, the geometric spacing or relation between successive fundamental channel frequencies is established such that none of the spurious signals associated with the generation of other higher or lower fundamental frequencies will be within the −70db limits of the rejection curves of the respective receivers, as typified by FIG. 4.

While the foregoing result might be obtained by a rather wide frequency spacing between successive fundamental channels, there is also the competing consideration of the desirability of spacing successive channels as closely as possible to maximize the number of channels within the available bandwidth. Accordingly, the optimum geometric relation between successive fundamental channels will be that which places the "closest" one of the potentially interfering spurious signals in the general-case example just beyond the −70db limits of the rejection curve, but which also minimizes the distance or frequency spacing of all of those potentially interfering spurious signals (in this instance 4) from the −70db rejection limits. In the FIG. 4 illustration, an additional margin (here ±27 kHz) has been provided between the −70db limits of rejection and the optimum "inner" limits of the respective spurious signals to accommodate various tolerances and drifts associated with the oscillators of the transmitter and receiver.

Reference is now made to FIG. 3 in which there is illustrated the general-case optimization of frequency spacing between a general-case fundamental frequency channel (X) and the several potentially-interfering spurious signals appearing in the illustrated embodiment. For purposes of discussion, those potentially interfering (but actually non-interfering) spurious signals are designated by the letter "S" followed by a signed numerical subscript, followed by a designation of that fundamental channel which is the source of the particular spurious signal. The numerical subscript indicates which 1/12th increment they are (i.e. 1, 2, etc.) above or below their respective fundamental frequency and the sign indicates above (higher) when plus and below (lower) when minus.

In the general-case example of FIG. 3, it will be noted that the $S_{+1}$ spurious signal for channel (X−23) and the $S_{-2}$ spurious signal for channel X+51 are substantially coincident with one another. Further, the $S_{+1}$ spurious signal for channel (X−23) refers to that spurious signal which results as the 13/12th increment of that fundamental channel which is 23 channels below that of fundamental channel (X) in the successive series of geometrically spaced channels. Similarly, the $S_{-2}$ spurious signal of channel (X+51) is that spurious signal which is the 10/12th increment of that fundamental channel which is 51 channels above channel (X) of the general-case example.

Above or to the right of the fundamental channel (X) in this optimized illustration of the general-case example, there are seen two other potentially interfering (but actually non-interfering) spurious signals which are closely spaced to one another and slightly beyond the required rejection limits of the associated receiver tuned to fundamental channel (X). One spurious signal is designated $S_{-1}$ of channel (X+25) and represents the 11/12th increment of that fundamental channel which is 25 channels above fundamental channel X. The other spurious signal is designated $S_{+2}$ of channel (X−43) and represents the 14/12th increment of that fundamental channel which is 43 channels below or lower in frequency than fundamental channel X.

The dotted-line spurious signal designated as $S_{+3}$ of channel (X−63) is included only for the purpose of illustrating that if the particular geometric spacing between successive fundamental channels was such as to permit 64 channels within the assigned band, there would exist a spurious signal from a fundamental channel which was 63 channels below the fundamental channel (X) and which would be so close in frequency to fundamental channel (X) as to cause cross-talking interference therewith. That would then suggest that the total number of successive channels bearing the same geometrical relationship to the preceding channel must not exceed 63 in number for the illustrated embodiment if one wishes to limit the general case study to the consideration of only the four spurious signals represented by $S_{\pm1}$ and $S_{\pm2}$ of any fundamental channel. Actually, in the illustrated example, only 61 channels will fit within the FCC-assigned 174–216 MHz band.

To obtain the optimized general-case example of FIG. 3, an iterative procedure of trial and error may be utilized to determine that geometric relationship or frequency multiplying factor between successive fundamental channels which provides the optimum frequency spacing between fundamental channel (X) and the four relevant spurious signals. Significant assistance in arriving at the optimum geometrical relationship is provided by knowing in advance, to a close approximation, the number of channels which are likely to exist in the assigned band. The limits to the frequency rejection curves of the successive receivers will determine some maximum number of channels. It should also be appreciated that the optimization of the general-case example will normally not result in the several relevant spurious signals all being coincicent with one another and equidistant from the fundamental channel (X). Therefore, some small additional frequency spacing or band between successive receivers must also be considered likely. It will be appreciated that the closest non-interfering spacing between channels is at the low end of the band and, because the rejection limits are the same for each receiver, the rejection zone between higher channels will increase, even though not required for avoidance of cross talk. With these guidelines one may approximate the number of channels which will be available and thereby establish an approximate initial value for the geometrical relationship between successive channels.

Figure 5:
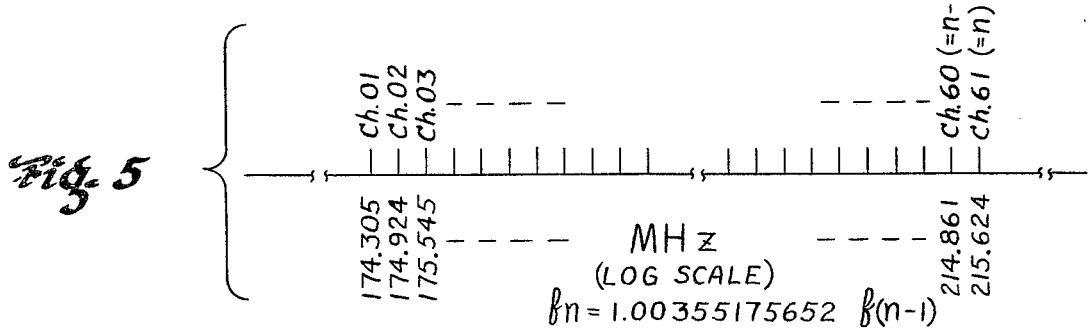
FIG. 5 illustrates the spacing of n telemetry channels on a logarithmic frequency scale within a predetermined band, the spacing having been determined in accordance with the general-case examples represented in FIGS. 3 and 4.

In the present example, one would approximate the number of channels to be about 61–62 which would, in turn, suggest an appropriate approximate multiplying factor for the frequency spacing of the successive channels. It should be noted that, with a constant geometric spacing between successive channels, a plot of those channels across the relevant frequency spectrum using a logarithmic scale for the frequency spectrum results in the successive plotted channels being equally spaced from one another, as illustrated in FIG. 5. By equally spacing the approximately 60 channels in the assigned band on a logarithmically-scaled frequency spectrum, one may conveniently measure the frequency intervals between several successive channels and develop an appropriate approximate multiplying factor between successive channels therefrom.

It remains, however, to optimize the general-case example which, as earlier noted, relies upon first determining and plotting the general-case using the approximate multiplying factor, then modifying that multiplying factor in one direction or another and re-plotting the general-case to determine the various frequency displacements of the spurious signals $S_{+1}$ and $S_{+2}$. Through a system of successive trials and errors, one is able to ultimately converge upon a multiplying factor which places the several relevant spurious signals must beyond the rejection band of a relevant receiver and which also minimizes the frequency displacement between the relevant spurious signal on either side of the fundamental channel (X), as in FIG. 3. More specifically, it has been observed that the frequency multiplying factor is an optimum value when the absolute frequency margin is maximized for whichever of the spurious components has the smallest frequency margin between each of the spurious components and the fundamental receiver channel. The following procedure may be used to find that optimum value of the frequency multiplying factor.

Firstly, an initial approximate multiplying factor is determined as previously mentioned. Then, using that approximate multiplying factor, a frequency spectrum representation of the general-case fundamental channel (X) and the four (in this embodiment) spurious signals closest in frequency thereto is generated or otherwise determined. From that general-case representation, the frequency margin of that spurious signal having the smallest frequency margin relative to the fundamental channel is determined and noted. The approximate multiplying factor is then modified by a relatively very small amount and the sequence repeated such that respective "smallest-margin spurious signals" may be compared. This process is repeated until the "smallest-margin spurious signal" having the largest margin relative to the fundamental channel is determined. The respective multiplying factor then represents the optimized value of the geometric relation between successive fundamental frequencies.

The sense (+ or −) in which the approximate multiplying values are modified may be guided by whether or not modification in one sense results in the "smallest-margin spurious signal" increasing its margin. If it does not, then the opposite sense is chosen.

As an alternative to or a simplification of the aforementioned method of optimization, the relative frequency margin between each of the closest spurious components and the fundamental receiver channel may be expressed mathematically by means of separate equations which are functions of the frequency multiplying factor $(\alpha+\Delta)$. As before, the purpose of this optimization is to find that value of the frequency multiplying factor which results in the largest absolute value of the frequency margins for whichever spurious component has the smallest frequency margin. In these equations, $\alpha$ is defined as the approximate multiplying factor, and $\Delta$ is a relatively very small perturbation which will be varied for the final optimization. Note that the equations are only valid over a narrow range; if $\Delta$ is given too large a value, new equations must be developed to show that a spurious component from some different channel has moved in closer to the fundamental channel.

For the particular embodiment illustrated, these four equations, one for each closest spurious component, are given below. Also, the resultant values are given (rounded to six places) if these equations are evaluated for $(\alpha+\Delta)=1.00355175652$.

| Component | Equation For Relative Frequency Margin From Fundamental | Evaluated For $(\alpha + \Delta) = 1.00355175652$ |
|---|---|---|
| S − 2 | $\frac{10}{12}(\alpha + \Delta)^{51} - 1$ | −.001502 |
| S − 1 | $\frac{11}{12}(\alpha + \Delta)^{25} - 1$ | +.001626 |
| S + 1 | $\frac{13}{12}(\alpha + \Delta)^{-23} - 1$ | −.001502 |
| S + 2 | $\frac{14}{12}(\alpha + \Delta)^{-43} - 1$ | −.001697 |

It is evident by examination of the equations that any further positive increase in the value of the $\Delta$ perturbation will cause the S−2 and S−1 locations to move upward in relative frequency, and the S+1 and S+2 locations to move downward in relative frequency. As shown in FIG. 3, such a positive perturbation will improve, or increase the absolute value of the frequency margin from the fundamental for the S−1 and S+1 components, but it will also degrade, or reduce the absolute value of the frequency margin from the fundamental for the S−2 and S+2 components.

In this example, it is apparent that the frequency multiplier value of $(\alpha+\Delta)=1.00355175652$ is an optimum solution, since any increase in this value will force the S−2 component closer to the fundamental frequency, and any decrease in this value will force the S+1 component closer to the fundamental frequency. The frequency margins for the remaining S−1 and S+2 components will also change, but they are larger, and, therefore, not of primary interest in the optimization.

It will be appreciated that the aforementioned processes of optimizing the multiplying factor or geometric relation between successive fundamental frequencies may be carried out in a variety of ways including graphical analysis, electro-mechanical analysis and/or electronic analysis. A variety of computers and appropriate programming techniques exist for practicing the process substantially entirely therewith in a manner well known by those skilled in the art.

By utilizing that aforementioned optimum multiplying factor to geometrically space successive channel frequencies, the optimized general-case depicted in FIG. 3 resulted. The uppermost scale beneath the FIG. 3 plot is calibrated in terms of frequency, relative to a unity value which is assigned to the fundamental channel X. The lowermost scale beneath the FIG. 3 plot is calibrated in terms of actual frequency wherein fundamental channel (X) is defined to be the first channel (i.e. CH 01) in the series which span the assigned band. Utilizing the optimum multiplying factor of 1.00355175652 and a first fundamental channel frequency of 174.305 MHz, it is possible to obtain 61 non-cross talking tentative channels within the 174-216 MHz band. The placement of these 61 tentative channels within the frequency spectrum is illustrated in FIG. 5 wherein channel 01 has an assigned frequency of 174.305 MHz; channel 02 has a frequency which is 1.00355175652 times 174.305 or, in other words, 174.924 MHz; channel 03 has a frequency of 175.545 MHz, and so on to channel n−1 (which in this case is channel 60) which has a frequency of 214.861 MHz and, finally, channel n (which is channel 61) having a frequency of 215.624 MHz.

The "n" (here 61) fundamental channels determined in accordance with the invention will be free of cross talk with one another from their various spurious signals resulting from the frequency multiplication harmonics; however, such channels are only tentatively available for ultimate selection inasmuch as other sources of interference and cross talk may prevent the use of certain frequencies. For instance, the 174-216 MHz band includes channels 7-13 of the commercial television band and certain ones of those TV channels may interfere with and prevent use of certain of the telemetry channels. Each telemetry installation will usually differ and be determined by those TV channels having significant strength in the locality. This conflict with TV channels and their sound, picture, and chroma carrier frequencies may greatly limit the number of available channels. Typically, between 15 and 25 telemetry channels remain available for selection for actual use. The telemetry system actually manufactured and installed is comprised of all or most of these 15-25 final channels.

Potential further interference to the use of some tentative channels due to possible response to image signals as a result of heterodyning is obviated by selecting the intermediate frequency in the receivers to be at least one-fourth (i.e. 10.7 MHz) of the bandwidth (i.e. 42 MHz) and then selecting the respective local oscillators in the lower half and the upper half respectively of the band to be that intermediate frequency respectively below and above their respective channel frequencies.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a telemetry system having a plurality of transmitter-receiver channels within a predetermined band, the fundamental frequency of each transmitter channel being different and being a constant multiple of a respective basic frequency whereby spurious signals resulting from various multiples of each said basic frequency are present and may cross talk to receiver channels tuned thereto, the improvement wherein each of the fundamental frequencies of said transmitter-receiver channels is a different one of at least some of the fundamental frequencies in a series of tentative fundamental frequencies, the successive fundamental frequencies in said series each having the same ratio to the immediately preceding fundamental frequency in said series.

2. The telemetry system of claim 1 wherein said same geometric relation between said fundamental frequencies is such that the frequencies of substantially all of said spurious signals differ sufficiently from substantially all of said receiver channels in said series to avoid cross talk therewith.

3. The telemetry system of claim 2 wherein the receiver of each said receiver channel has predetermined rejection curve frequency limits, and said same said ratio between said fundamental frequencies comprises a multiplying factor which is approximately that which would provide within said predetermined band the maximum number of receiver channels for which the respective said rejection curve limits are non-overlapping.

4. The telemetry system of claim 2 wherein each said basic frequency is multiplied by a factor of 12 to obtain the respective said transmit channel fundamental frequency, the relation of the upper-end frequency to the lower-end frequency of said predetermined band is about 1.25 to 1 such that said spurious signals within the range of 10/12th to 14/12th of the various said fundamental frequencies may occur within said predetermined band, and said same said ratio between said fundamental frequencies comprises a multiplying factor of substantially 1.00355175652.

5. The telemetry system of claim 4 wherein said predetermined band is 174 to 216 MHz and said tentative fundamental frequencies provide 61 tentative channels.

6. The telemetry system of claim 5 wherein said fundamental frequencies comprise only said tentative channels for which the respective receiver is also substantially free of cross talk and interference from other sources than said spurious signals.

7. In the manufacture of a telemetry system having a plurality of transmitter-receiver channels within a predetermined band, the fundamental frequency of each transmitter channel being different and being a constant multiple of a respective basic frequency whereby spurious signals resulting from various multiples of each said basic frequency are present and may cross talk to receiver channels tuned thereto, the method of selecting the fundamental frequencies of said transmitter-receiver channels comprising:

predetermining a series of tentative fundamental frequencies, the successive fundamental frequencies in said series each having the same ratio to the immediately preceding fundamental frequency in said series whereby determination of said ratio between frequencies is facilitated; and selecting said fundamental frequencies of the respective transmitter-receiver channels only from said predetermined series of tentative fundamental frequencies.

8. The method of manufacturing the telemetry system of claim 7 wherein said step of predetermining comprises choosing as said ratio between successive fundamental frequencies that geometric relation for which substantially all of said spurious signals differ sufficiently from substantially all of said receiver channels in said series to avoid cross talk therewith.

9. The method of manufacturing the telemetry system of claim 8 wherein each said receiver channel has predetermined rejection curve frequency limits and said choosing of said ratio between successive fundamental frequencies comprises:

a. initially determining an approximate multiplying factor between successive fundamental frequencies which is approximately that which would provide, within said predetermined band, the maximum number of receiver channels for which the respective said rejection curve limits are non-overlapping;

b. generating a frequency spectrum representation of a general-case fundamental channel and a predetermined number of said spurious signals closest in frequency to said generalcase fundamental channel, the frequencies of said spurious signals being a function of said approximate multiplying factor;

c. determining the frequency margin of that said spurious signal representation of said predetermined number having the smallest frequency margin relative to said generalcase fundamental channel;

d. comparing said determined frequency margin with the largest said determined frequency margin previously measured;

e. modifying said approximate multiplying factor by a relatively very small value and repeating steps b, c, and d; and f. repeating step e until a maximum in said determined frequency margin is recognized, the respective said multiplying factor therefor comprising said geometric relation between successive fundamental frequencies.

* * * * *